(12) United States Patent
Miura et al.

(10) Patent No.: US 7,884,241 B2
(45) Date of Patent: Feb. 8, 2011

(54) DISTILLATION PROCESS

(75) Inventors: Hiroyuki Miura, Himeji (JP);
Kenichiro Kawazumi, Himeji (JP)

(73) Assignee: Daicel Chemical Industries, Ltd., Sakai-shi (JP)

( * ) Notice: Subject to any disclaimer, the term of this patent is extended or adjusted under 35 U.S.C. 154(b) by 120 days.

(21) Appl. No.: 11/791,326

(22) PCT Filed: Dec. 5, 2005

(86) PCT No.: PCT/JP2005/022713

§ 371 (c)(1),
(2), (4) Date: May 23, 2007

(87) PCT Pub. No.: WO2006/062216

PCT Pub. Date: Jun. 15, 2006

(65) Prior Publication Data

US 2008/0214866 A1    Sep. 4, 2008

(30) Foreign Application Priority Data

Dec. 6, 2004    (JP) .............................. 2004-352842

(51) Int. Cl.
   *C07C 51/42*   (2006.01)
(52) U.S. Cl. .................................... 562/608
(58) Field of Classification Search ............... None
   See application file for complete search history.

(56) References Cited

U.S. PATENT DOCUMENTS

| | | | |
|---|---|---|---|
| 3,772,156 A | 11/1973 | Johnson et al. | |
| 4,008,131 A | 2/1977 | Price | |
| 4,029,553 A | 6/1977 | Price | |
| 4,094,962 A * | 6/1978 | Cocuzza et al. | 423/576.4 |
| 5,374,774 A | 12/1994 | Ochiai | |
| 6,066,762 A * | 5/2000 | Yoneda et al. | 562/519 |
| 6,175,039 B1 * | 1/2001 | Voss | 562/519 |

FOREIGN PATENT DOCUMENTS

| | | |
|---|---|---|
| EP | 0 696 565 A1 | 2/1996 |
| GB | 1 350 726 | 11/1971 |
| JP | 52-23016 | 2/1977 |
| JP | 6-40999 A | 2/1994 |
| JP | 06040999 * | 2/1994 |
| JP | 2005289936 * | 10/2005 |

OTHER PUBLICATIONS

Machine translation of JP 2005289936.*

* cited by examiner

*Primary Examiner*—Karl J Puttlitz
(74) *Attorney, Agent, or Firm*—Birch, Stewart, Kolasch & Birch, LLP

(57)    ABSTRACT

A mixture containing hydrogen iodide and water and having a water content of not more than 5% by weight (particularly not more than 3% by weight) in a distillation system is distilled to prevent condensation of hydrogen iodide in the distillation system. The mixture may comprise hydrogen iodide, water, methanol, methyl iodide, acetic acid, and methyl acetate. Even when the mixture contains hydrogen iodide at a concentration of 1 to 3000 ppm on the basis of weight, an acetic acid product having a concentration of hydrogen iodide of not more than 50 ppm can be obtained by withdrawing a fraction containing hydrogen iodide from the top of the column, and withdrawing acetic acid as a side-cut stream or a stream from the bottom of the column. Such a process (distillation process) effectively inhibits condensation of hydrogen iodide in the distillation system and corrosion in the distillation system.

15 Claims, 2 Drawing Sheets

DISTILLATION PROCESS

TECHNICAL FIELD

The present invention relates to a process (e.g., a distillation process, and a production process of acetic acid) useful for inhibiting condensation of hydrogen iodide in a distillation column, reducing corrosion of a distillation column, and decreasing a concentration of hydrogen iodide in a bottom solution or a side stream solution of a distillation column.

BACKGROUND ART

In a production of acetic acid, when a solution containing water, hydrogen iodide, methyl iodide, methyl acetate, acetic acid, and others is distilled for purification, hydrogen iodide forms an azeotrope with water. As a result, hydrogen iodide is condensed in a distillation column, thereby it is difficult to efficiently remove hydrogen iodide even when the mixture is distilled. Moreover, in the case where the concentration of hydrogen iodide in a distillation column is high, corrosion of the column body is accelerated.

Therefore, in order to reduce the concentration of hydrogen iodide in the distillation column, it has been proposed to convert hydrogen iodide into methyl iodide by feeding (or introducing) a component such as methanol to a middle plate of the distillation column.

Japanese Patent Application Laid-Open No. 40999/1994 (JP-6-40999A) (Patent Document 1) discloses a process for producing acetic acid, which comprises supplying methanol and carbon monoxide to a carbonylation zone that holds a liquid reaction composition consisting of a rhodium catalyst, methyl iodide, an iodide salt, water having a content up to about 10% by weight, methyl acetate having a concentration of at least 2% by weight, and acetic acid; introducing the liquid reaction composition into a flash zone; and recycling a liquid component from the flash zone to the reaction zone and collecting an acetic acid product from a vapor fraction of the flash zone by using simple distillation; wherein the vapor fraction from the flash zone is introduced into the distillation zone, a light end stream to be recycled is removed from the top of the distillation zone, and an acid stream which has a water content of less than 1500 ppm and a propionic acid concentration of less than 500 ppm is withdrawn from the distillation zone. The document also mentions that an iodide as an impurity is removed from the acetic acid product by passing the acetic acid product through an ion-exchange resin (anion-exchange resin) bed. Further, this document describes that increase of the hydrogen iodide component is inhibited by introducing a small amount of methanol into the distillation zone (preferably the lower part of the supplying point thereof), converting hydrogen iodide into methyl iodide, and removing the converted matter into the light end stream to be recycled; that the process can treat hydrogen iodide up to 5000 ppm in the feeding matter; and that a relatively high concentration of methyl acetate in the distillation zone converts hydrogen iodide into methyl iodide by applying the distillation zone at a sufficiently high pressure to remove methyl iodide into the light end stream to be recycled.

However, even in these processes, since removal of hydrogen iodide depends on a reaction with methanol or methyl acetate, hydrogen iodide cannot be efficiently removed. Moreover, it is not preferred to increase the pressure for converting hydrogen iodide into methyl iodide, because corrosion due to hydrogen iodide is promoted. Incidentally, even in the case of removing the acetic acid product containing water of not more than 1500 ppm, the concentration of hydrogen iodide in the acetic acid product cannot be greatly reduced because of affinity between hydrogen iodide and water. Furthermore, in order to further reduce the concentration of hydrogen iodide, an anion-exchange resin is required, and as a result, processing cost increases.

Japanese Patent Application Laid-Open No. 23016/1977 (JP-52-23016A) (Patent Document 2) discloses a process for removing and collecting an iodine-containing component and drying acetic acid, which comprises introducing an acetic acid stream containing water, methyl iodide, and hydrogen iodide into a middle point of a first distillation zone, removing a major portion of methyl iodide and a part of water from the top of the first distillation zone, removing a major portion of hydrogen iodide from the bottom of the first distillation zone, withdrawing a stream from a center part of the first distillation zone to introduce the withdrawn stream into an upper part of a second distillation zone, introducing a methanol stream into a lower part of the second distillation zone, removing a stream containing the residual water and methyl iodide which are coexistent with methyl acetate from the top of the second distillation zone, and withdrawing a stream comprising an acetic acid product, which is substantially dried and substantially free from hydrogen iodide and methyl iodide, from the bottom or near the bottom of the second distillation zone. This document also discloses that, in a process for recovering acetic acid by distilling a side-cut fraction from the first distillation column in the second distillation column, it is unnecessary to recycle a fraction containing hydrogen iodide as the side-cut fraction of the second distillation column to the first distillation column by introducing methanol into the second distillation column and chemically removing hydrogen iodide.

However, in order to reduce the concentration of hydrogen iodide, methanol introduced into the second distillation column is necessary to be reacted with hydrogen iodide. Accordingly, it is difficult to efficiently reduce the concentration of hydrogen iodide with simple distillation operation.

Great Britain Patent No. 1350726 specification (Patent Document 3) discloses a purification process of a monocarboxylic acid component containing water and alkyl halide and/or hydrogen halide contaminants, which the process comprises introducing a monocarboxylic acid component containing water and alkyl halide and/or hydrogen halide contaminants into the upper half of a distillation zone, removing an overhead fraction containing a major proportion of water and the alkyl halide, removing a stream from the middle portion of the zone and below the point of the introduction to eliminate a major proportion of hydrogen halide present in the zone, and removing a product monocarboxylic acid stream from the bottom part of the zone, the product acid stream being substantially dry and substantially free of any alkyl halide and hydrogen halide contaminants. The document describes that a concentration of hydrogen halide peaks in the middle portion of the distillation column where the liquid composition of carboxylic acid has a water content from about 3 to 8 percents, and if a side stream is withdrawn from the middle portion of the distillation column, a monocarboxylic acid in which almost all of hydrogen halide is removed can be obtained. Further, the document also discloses that in the case where a reaction product obtained from a reaction of methanol with carbon monoxide is subjected to a flash distillation, and a fraction separated by the flash distillation is introduced into the distillation column, hydrogen iodide is condensed in a side stream from the middle portion of the distillation column and removed.

However, in such a process, not only irregular distillation off of hydrogen iodide from a bottom solution or side stream cannot be avoidable because of fluctuation of the peak position of hydrogen halide concentration due to variable factors (such as temperature, and pressure) in the distillation step, but also the quality of acetic acid sometimes fluctuates because of contamination with hydrogen iodide of an acetic acid product. Further, due to affinity between hydrogen iodide and water, there is a limit to reduce the hydrogen iodide concentration in the acetic acid product.

Patent Document 1: JP-6-40999A (Claims, and Paragraph No. [0043])

Patent Document 2: JP-52-23016A (Claims, the lower right column of page 5, the lower light column to the lower right column of page 7, and Example 1)

Patent Document 3: Great Britain Patent No. 1350726 specification (Claims, page 2, lines 66-76, and Example 1)

DISCLOSURE OF THE INVENTION

Problems to be Solved by the Invention

It is therefore an object of the present invention to provide a process (a distillation process) for effectively preventing condensation of hydrogen iodide in a distillation system and inhibiting corrosion in the distillation system.

Another object of the present invention is to provide a process (a distillation process) which ensures to effectively inhibit contamination with hydrogen iodide of a bottom solution or a side stream component (e.g., an acetic acid product) in a distillation column, and stabilize the quality of the bottom solution or the side stream component.

It is still another object of the present invention to provide a process (a distillation process) which ensures to purify a carboxylic acid such as acetic acid with high purity.

Means to Solve the Problems

The inventors of the present invention made intensive studies to achieve the above objects and finally found that distillation of a mixture containing hydrogen iodide and water under a condition of a low water content realizes effective removal of hydrogen iodide from a distillation system. The present invention was accomplished based on the above findings.

That is, the process of the present invention is a process for distilling a mixture containing hydrogen iodide and water, which comprises distilling the mixture having a water content of not more than 5% by weight (e.g., not more than 3% by weight) in a distillation system to prevent condensation of hydrogen iodide in the distillation system. The process is applicable for various mixtures containing hydrogen iodide and water, and for example, is applicable for a mixture containing hydrogen iodide, water, an alcohol having a carbon number of "n", an alkyl iodide corresponding to the alcohol, a carboxylic acid having a carbon number of "n+1", and an ester of the carboxylic acid with the alcohol. Also in this process, the condensation of hydrogen iodide in the column can be inhibited by distilling the mixture while maintaining the water content of not more than 5% by weight in the distillation column.

The present invention also includes a process for producing acetic acid which comprises distilling a mixture containing hydrogen iodide, water, methanol, methyl iodide, acetic acid and methyl acetate in a water content of not more than 5% by weight in a distillation column, withdrawing a fraction containing hydrogen iodide (an overhead fraction) from the top of the column, and withdrawing acetic acid as a side-cut stream by side-cut or a stream (a bottom solution) from the bottom (or the bottom part) of the column, and a process for producing acetic acid which comprises distilling the mixture in a water content of not more than 5% by weight in a distillation column, withdrawing a fraction containing hydrogen iodide (an overhead fraction) from the top of the column, and withdrawing acetic acid as a side-cut stream by side-cut or a stream (a bottom solution) from the bottom of the column to reduce the concentration of hydrogen iodide to not more than 50 ppm in said acetic acid.

In these processes, the mixture may contain hydrogen iodide at a concentration of 1 to 3000 ppm on the basis of weight. Moreover, a suitable component having a reactivity to hydrogen iodide (for example, at least one component selected from the group consisting of methyl acetate and an alkali metal hydroxide) may be introduced into the distillation column, and the mixture may be distilled while maintaining the water content of not more than 5% by weight in the distillation column.

Effects of the Invention

According to the present invention, distillation under a condition of a specific water content effectively prevents condensation of hydrogen iodide in a distillation system, and inhibits corrosion of the distillation system. Moreover, since hydrogen iodide can be effectively removed from the distillation system, contamination with hydrogen iodide of a bottom solution or a side stream component obtained from the distillation column can be effectively inhibited even when hydrogen iodide is a slight amount, as a result the quality of the bottom solution or the side stream component can be stabilized. Therefore, a carboxylic acid such as acetic acid can be purified at a high purity by utilizing such a process. Further, introduction of at least one component selected from the group consisting of methanol, methyl acetate and an alkali metal hydroxide into a distillation column ensures not only further effective removal of hydrogen iodide but also reduction of the amount to be used of the component. Accordingly the present invention can also reduce energy consumption or the amount of waste products.

DETAILED DESCRIPTION OF THE INVENTION

Figure 1:
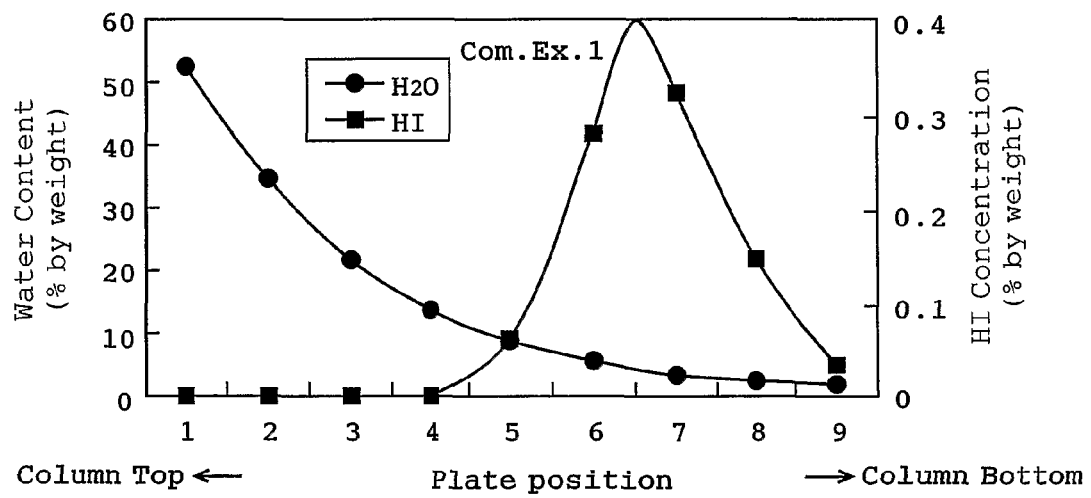
FIG. 1 is a graph showing the distribution of the water content and the concentration of hydrogen iodide in the column of Comparative Example 1.

The present invention is applied to distillation of a mixture containing hydrogen iodide and water. This mixture is not particularly limited to a specific one as long as the mixture substantially contains hydrogen iodide and water. For example, the mixture may contain, in addition to hydrogen iodide and water, at least one member selected from the group consisting of an alcohol, an alkyl iodide, a carboxylic acid or an acid anhydride thereof, and an alkyl ester of a carboxylic acid (e.g., at least one member selected from the group consisting of an alcohol having a carbon number of "n", an alkyl iodide corresponding to the alcohol, a carboxylic acid having a carbon number of "n+1" or an acid anhydride thereof, and an ester of the carboxylic acid with the alcohol).

The typical mixture may include a reaction mixture which is obtained from a carbonylation reaction of an alcohol having a carbon number of "n" with carbon monoxide, and the mixture which contains a carboxylic acid having a carbon number of "n+1" or an acid anhydride thereof. Moreover, the mixture usually contains at least one member selected from the group consisting of water, an alcohol having a carbon number of "n", an alkyl iodide corresponding to the alcohol, a carboxylic acid having a carbon number of "n+1" or an acid anhydride thereof, and an ester of the carboxylic acid with the alcohol in many cases. The reaction mixture may be obtained, for example, by allowing an alcohol having a carbon number of "n" (e.g., methanol) to react with carbon monoxide to produce a carboxylic acid (e.g., acetic acid) or an acid anhydride thereof having a carbon number of "n+1" in the presence of a liquid reaction composition comprising a limited amount of water, a carbonylation catalyst (e.g., a catalyst composed of a metal of the group VIII of the Periodic Table of Elements, such as a rhodium catalyst and/or an iridium catalyst), an iodide salt soluble in the liquid reaction composition [for example, a stabilizer, a co-catalyst or an accelerator, such as an alkali metal iodide (e.g., lithium iodide, potassium iodide, and sodium iodide)], an alkyl iodide (e.g., an alkyl iodide such as methyl iodide, ethyl iodide, or propyl iodide) and a carboxylic acid ester (e.g., methyl acetate, and ethyl propionate).

The water content in the liquid reaction composition may be, for example, about 0.1 to 14% by weight (e.g., about 0.1 to 10% by weight), preferably about 1 to 10% by weight, and more preferably about 1 to 5% by weight, and may be about 0.1 to 7% by weight (e.g., about 0.1 to 5% by weight).

The carbonylation catalyst may be also used in the form of a halide (e.g., a chloride, a bromide, and an iodide), a carboxylic acid salt (e.g., an acetate), a salt of an inorganic acid (e.g., a sulfate, a nitrate, and a phosphate), a complex or a complex salt. The preferred metal catalyst includes a rhodium catalyst. The proportion of the carbonylation catalyst may be, for example, about 50 to 5000 ppm, preferably about 100 to 4000 ppm, more preferably about 500 to 2000 ppm, and usually about 500 to 1500 ppm in the liquid reaction composition (liquid phase). The content of the iodide salt in the liquid reaction composition may be, for example, about 0.1 to 40% by weight (e.g., about 0.5 to 35% by weight), preferably about 1 to 30% by weight (e.g., about 2 to 20% by weight), and more preferably about 5 to 15% by weight, and may be about 10 to 20% by weight. Further, the concentration of the alkyl iodide may be about 1 to 25% by weight (e.g., about 1 to 20% by weight), preferably about 2 to 20% by weight (e.g., about 3 to 15% by weight), and more preferably about 5 to 16% by weight (e.g., about 5 to 15% by weight). The concentration of the carboxylic acid ester may be about 0.1 to 20% by weight, preferably about 0.5 to 15% by weight, and more preferably about 0.5 to 6% by weight (e.g., about 2 to 6% by weight).

Carbon monoxide to be supplied to the reaction system may be used as a pure gas, or diluted with an inactive gas (e.g., nitrogen, helium, and carbon dioxide). Moreover, a waste gas component containing carbon monoxide obtained from the succeeding step (e.g., a distillation step (distillation column)) may be recycled to the reaction system. The partial pressure of carbon monoxide in the reaction system may be, for example, about 0.8 to 3 MPa, preferably about 1.15 to 2.5 MPa, and more preferably about 1.15 to 2 MPa (e.g., about 1.18 to 2 MPa) as an absolute pressure. Incidentally, carbon monoxide may be supplied by sparging from a lower part of a reactor.

In the carbonylation reaction, hydrogen may be supplied to the reaction system. The hydrogen may be supplied to the reaction system as a mixed gas together with carbon monoxide which is a raw material. The partial pressure of hydrogen in the reaction system may be, for example, about 0.01 to 0.1 MPa, preferably about 0.014 to 0.07 Mpa (e.g., about 0.015 to 0.05 MPa), and more preferably about 0.02 to 0.04 MPa as an absolute pressure.

In the carbonylation reaction, the reaction temperature may be, for example, about 100 to 250° C., preferably about 150 to 220° C., and more preferably about 170 to 210° C. Moreover, the reaction pressure may be about 1 to 5 MPa, preferably about 1.5 to 4 MPa, and more preferably about 2 to 3.5 MPa as an absolute pressure.

The reaction may be carried out in the presence or absence of a solvent. As the reaction solvent, a variety of solvents may be used, and a carboxylic acid (e.g., acetic acid) being a product is usually employed.

The reaction mixture produced by such a carbonylation reaction contains water, an alcohol (e.g., methanol), an alkyl iodide corresponding to the alcohol (e.g., methyl iodide), a carboxylic acid having a carbon number of "n+1" (e.g., acetic acid) or an acid anhydride thereof (e.g., acetic anhydride), and an ester of the carboxylic acid with the alcohol (e.g., methyl acetate). Further, the reaction mixture contains a by-product, for example, hydrogen iodide, a carboxylic acid having a carbon number of not less than "n+2" (e.g., propionic acid) or an acid anhydride thereof, an aldehyde (e.g., acetaldehyde, and crotonaldehyde) in many cases.

The present invention may be also applied to such a reaction mixture (or liquid reaction composition). The present invention may be also applied to a light component or fraction in the reaction mixture (or liquid reaction composition) separated by a first distillation (a distillation by a plate column, a packed column, a flash distillation column, or others). The light component or fraction is rich in a lower-boiling component(s) such as water, an alcohol, an alkyl iodide, a carboxylic acid or an acid anhydride thereof, a carboxylic acid ester and/or hydrogen iodide. Thus, the present invention is useful for separation and purification of a carboxylic acid or an acid anhydride thereof. That is, the reaction mixture (or liquid reaction composition) is usually continuously withdrawn from a carbonylation reactor, supplied to a flash distillation zone under a heated or unheated condition, separated into a light component or fraction (vapor component) rich in the lower-boiling component, and a heavy component (liquid component) rich in a higher-boiling component(s) such as a rhodium catalyst, an iodide salt, and/or a carboxylic acid having a carbon number of "n+2". The light component is subjected to a second distillation as a mixture, and the heavy component is recycled to the carbonylation reactor. Among the flash distillations, in an adiabatic flash distillation the reaction mixture can be separated into a vapor component and a liquid component by depressurization without heating, and in an isothermal flash distillation the reaction mixture can be separated into a vapor component and a liquid component by heating and depressurization. The reaction mixture may be separated by combining these flash conditions. Such a flash distillation may be, for example, performed at a temperature of about 80 to 200° C. and a pressure (absolute pressure) of about 50 to 1000 kPa (for example, about 100 to 1000 kPa), preferably about 100 to 500 kPa, and more preferably about 100 to 300 kPa.

The light component sometimes contains a slight amount of a by-product (e.g., an aldehyde such as acetaldehyde, and a carboxylic acid having a carbon number of "n+2", such as propionic acid) in addition to water, the alcohol, the alkyl iodide, the carboxylic acid or an acid anhydride thereof, the carboxylic acid ester and/or hydrogen iodide. After subjecting such a light component as a mixture to the second distillation, a purified carboxylic acid or an acid anhydride thereof can be obtained.

Incidentally, since hydrogen iodide can be efficiently removed or distilled off in the present invention, the concentration of hydrogen iodide (on the basis of weight) in the mixture is not particularly limited to a specific one, and for example, may be selected from the range of about 1 to 3000 ppm, and may be usually about 10 to 2000 ppm, preferably about 20 to 1500 ppm, and more preferably about 30 to 1200 ppm (e.g., about 50 to 1000 ppm).

Figure 2:
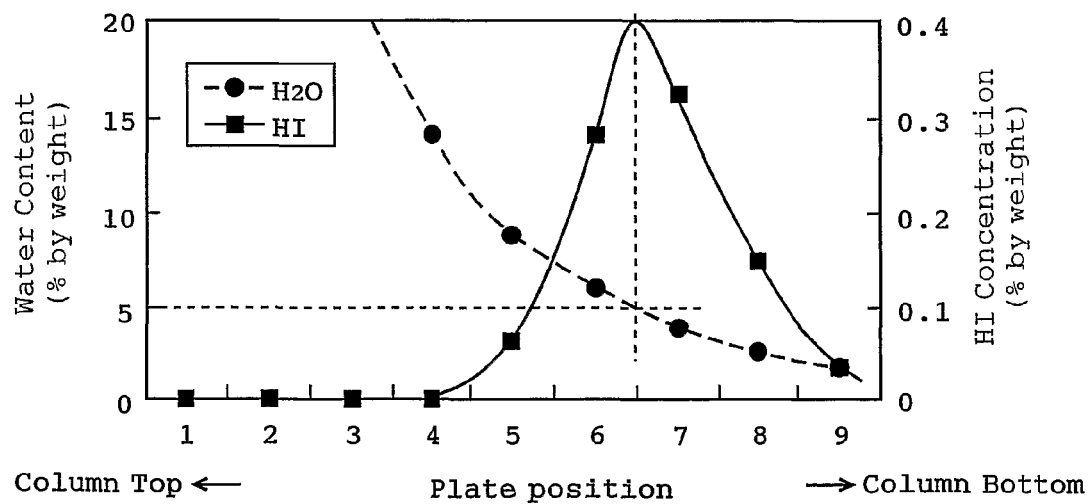
FIG. 2 is a magnified graph regarding the water content in FIG. 1.

In the step for distilling the mixture containing water and hydrogen iodide, when the water content in the distillation system (or distillation column) (in practice, the water content in the liquid phase of the distillation system, or the water content in the top of the column) is high, hydrogen iodide remains and is condensed, as a result, hydrogen iodide cannot be efficiently removed. More specifically, according to the research about the relationship among the water content, the concentration of hydrogen iodide (HI concentration), and the number of plates of a plate column for the distillation system, as shown in FIG. 1 and FIG. 2, in the distillate, even when the water content is reduced, the concentration of hydrogen iodide therein is not simply increased and shows a peak with a central focus on the water content of about 5% by weight. In the case where the water content in the top of the plate column exceeds 5% by weight, therefore, the peak of the hydrogen iodide concentration is positioned or distributed below the top of the column and hydrogen iodide is condensed in the distillation column. On the other hand, when the water content in the top of the plate column is not more than 5% by weight, the peak of the hydrogen iodide concentration is positioned or distributed above the top of the column and hydrogen iodide can be efficiently removed from the top of the column.

Therefore, in the present invention, distillation is carried out under a condition that the water content in the distillation system (distillation column or distillation zone) (a water content in a liquid phase or a mixture to be introduced into the distillation column, particularly, a water content in the top of the column) is not more than 5% by weight (e.g., about 0.1 to 4% by weight), preferably not more than 4% by weight (e.g., about 0.2 to 4% by weight), more preferably not more than 3% by weight (about 0.3 to 3% by weight), and particularly about 0.5 to 2.5% by weight (e.g., about 0.5 to 2% by weight). The distillation with keeping or holding such a water content ensures to efficiently remove or withdraw a fraction having a high concentration of hydrogen iodide from the top of the column, to effectively inhibit condensation of hydrogen iodide in the distillation system (or distillation column, distillation zone), and to prevent corrosion in the distillation system (or distillation column, distillation zone). Furthermore, since even when variable factors such as pressure fluctuation act on the distillation system, the peak position of hydrogen iodide concentration fluctuates in the overhead zone, the remanence of hydrogen iodide in the distillation system can be remarkably inhibited.

Incidentally, in the distillation of the above-mentioned reaction mixture (or liquid reaction composition), particularly the light fraction, a carboxylic acid (e.g., acetic acid) or an acid anhydride thereof (e.g., acetic anhydride) can be withdrawn as a bottom solution from the bottom (column bottom) of the distillation system, or as a side stream from the side part of the distillation system by side-cut, and usually as a side stream from the side part of the distillation system by side-cut in many cases. In the case where a carboxylic acid (e.g., acetic acid) or an acid anhydride thereof (e.g., acetic anhydride), particularly a carboxylic acid (e.g., acetic acid) is distilled under the above-mentioned condition, a fraction (e.g., acetic acid) from which hydrogen iodide is mostly removed can be withdrawn as a bottom solution from the column bottom, or as a side stream solution obtained by side-cut, and contamination with hydrogen iodide or others can be effectively inhibited.

The number of plates of the distillation system or distillation column is not particularly limited to a specific one. When the number of plates is "m", the bottom solution from the column bottom or the fraction (side stream) obtained by side-cut can be withdrawn from the bottom (column bottom) of the distillation system or the distillation column, or withdrawn from the range of the first plate from the bottom to the ("m"× ⅔)th plate from the bottom [e.g., the first plate from the bottom to the ("m"×½)th plate from the bottom]. Incidentally, since the theoretical plate number of the plate column corresponds to an equivalent theoretical plate number of the packed column, the number of plates in the plate column can be read as the equivalent plate number for the case of packed column.

Moreover, a distillate (a fraction containing water, methyl iodide, and/or others) from the top of the distillation system or the distillation column may be separated into an upper layer having a high water content and a lower layer rich in methyl iodide, and the upper layer may be used for reflux in the distillation column. In the case where acetic acid is distilled and purified while refluxing the upper layer, accumulation of hydrogen iodide proceeds, and thereby, corrosion of the distillation column body is accelerated. Therefore, in order to effectively remove hydrogen iodide, it is useful to reflux at least the lower layer rich in methyl iodide among the distillate from the top of the column. Both the lower layer rich in methyl iodide and the upper layer having a high water content may be utilized for refluxing. The concentration of methyl iodide in the reflux solution is, for example, about 50 to 90% by weight, and preferably about 65 to 85% by weight. In such a reflux operation, the amount of the reflux may be equal or more (e.g., about 1.5 to 10 times), and preferably not less than twice (e.g., 2 to 5 times) relative to an amount of flow of the layer (lower layer) to be distilled.

The water content in the distillation system may be adjusted by a distillation condition. The distillation condition may be selected depending on the species of a compound to be separated and purified. For example, in the case of acetic acid, the temperature in the top of the column may be about 78 to 120° C., preferably 79 to 110° C., and more preferably 80 to 105° C. The pressure (absolute pressure) may be about 10 to 400 kPa, preferably about 100 to 350 kPa (e.g., about 150 to 300 kPa), and more preferably 170 to 290 kPa.

Further, the water content in the distillation system may be decreased or adjusted by adding other component to the distillation system. For example, in purification of acetic acid or the like, the mixture may be distilled by introducing at least one component selected from the group consisting of methanol, methyl acetate and an alkali metal hydroxide (e.g., lithium hydroxide, potassium hydroxide, and sodium hydroxide) at an appropriate place of the distillation column (for example, at the bottom part, or between the bottom part and the middle (or intermediate) part) for maintaining or keeping the water content of not more than 5% by weight in the distillation column. Such a process can remove hydrogen iodide, and decrease the amount to be used of the above component(s) such as methanol, methyl acetate and/or the alkali metal (e.g., potassium hydroxide), and in addition, reduce energy consumption or the amount of waste products.

The amount of the above component(s) to be introduced may be, for example, about 1 to 200 parts by weight (e.g., about 3 to 150 parts by weight) and preferably about 5 to 100 parts by weight relative to 100 parts by weight of the distillate from the top of the column.

Incidentally, as the distillation system, a conventional distillation apparatus, for example, a plate column, or a packed column is available. The process of the present invention may be carried out by a batch system in which a given amount of the mixture is fed to the distillation system and distilled, a semi-batch system, or a continuous system in which a given amount of the mixture is distilled while continuously introducing the mixture into the distillation system.

Such a process can greatly reduce the concentration of hydrogen iodide in the bottom solution or the side stream solution (e.g., acetic acid stream). The concentration of hydrogen iodide in the bottom solution or the side stream solution (e.g., purified acetic acid) may be usually not more than 50 ppm (e.g., about 1 ppb to 10 ppm), not more than 10 ppm (about 0.001 to 1 ppm), and particularly not more than 1 ppm (about 0.001 to 0.1 ppm) on the basis of weight.

Incidentally, the distillate rich in hydrogen iodide distilled from the column top of the distillation system (the distillate from the top of the column) sometimes contains a lower-boiling component (or lower-boiling components) such as an alcohol (e.g., methanol), an alkyl iodide (e.g., methyl iodide), and/or an alkyl ester of a carboxylic acid (e.g., methyl acetate). Therefore, such a distillate may be further distilled for separating into a fraction rich in hydrogen iodide and a useful component [e.g., an alcohol (e.g., methanol), an alkyl iodide (e.g., methyl iodide), an alkyl ester of a carboxylic acid (e.g., methyl acetate)] and the useful component may be circulated to the reaction system. Moreover, from the bottom of the distillation system or the column bottom, a component having a higher-boiling component (or higher-boiling components) such as a carboxylic acid having a carbon number of "n+2", or an aldehyde (e.g., acetaldehyde, and crotonaldehyde) is sometimes discharged together with a carboxylic acid having a carbon number of "n+1" or an acid anhydride thereof. Such a higher-boiling component may be further separated by distillation for recovering a carboxylic acid having a carbon number of "n+1" n or an acid anhydride thereof as a product, or for circulating to the reaction system.

INDUSTRIAL APPLICABILITY

The present invention is useful for separating hydrogen iodide from a system where water and hydrogen iodide coexist, e.g., for producing a purified carboxylic acid by removing a by-product hydrogen iodide in production of a carboxylic acid such as acetic acid.

EXAMPLES

The following examples are intended to describe this invention in further detail and should by no means be interpreted as defining the scope of the invention.

Comparative Example 1

A distillation was carried out as follows: a liquid mixture containing 34% by weight of methyl iodide, 9.8% by weight of methyl acetate, 1.2% by weight of water and 55% by weight of acetic acid, and having a hydrogen iodide concentration of 190 ppm by weight was fed at a feed rate of 26 kg/h to the bottom part of a plate column having 9 plates, a side-cut solution was withdrawn from the 9th plate from the top of the column at a side-cut rate of 15.2 kg/h, and a bottom solution was withdrawn at a rate of 0.65 kg/h (the pressure of the top of the column: 230 kPa, and the temperature of the top of the column: 98° C.). Incidentally, the distillate from the top of the column was separated into an upper layer and a lower layer, and the upper layer was refluxed at a reflux rate of 3.3 kg/h. Whole of the lower layer was distilled off.

As a result, the water content in the top plate of the column was 53% by weight, and hydrogen iodide was condensed to about 2000 ppm by weight in the 6th and the 7th plates (having a water content of 3.8 to 5.8% by weight) from the top of the column. The concentration of hydrogen iodide in the acetic acid distillate withdrawn from the side-cut was 3000 ppm. FIG. 1 and FIG. 2 show the distribution of the water content and the concentration of hydrogen iodide (HI concentration) in the column. Incidentally, FIG. 2 is a magnified graph regarding the water content of FIG. 1.

Example 1

A distillation was carried out as follows: the liquid mixture used in Comparative Example 1 was fed at a feed rate of 26 kg/h to the bottom part of a plate column having 8 plates, a side-cut solution was withdrawn from the 8th plate from the top of the column at a side-cut rate of 14.5 kg/h, and a distillate from the top of the column was withdrawn at a flow rate of 10.9 kg/h (the pressure of the top of the column: 240 kPa, and the temperature of the top of the column: 79° C.). Incidentally, the distillate from the top of the column was separated into an upper layer and a lower layer, and a mixture of the lower layer and the upper layer (methyl iodide concentration of 77% by weight) was refluxed at a reflux ratio of 2.35.

Figure 3:
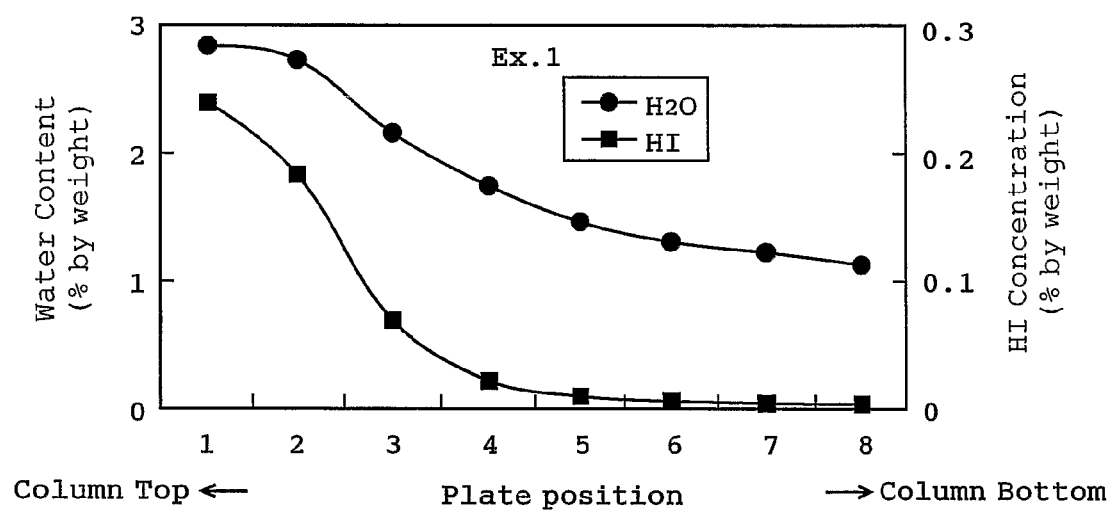
FIG. 3 is a graph showing a relationship among the water content, the concentration of hydrogen iodide, and the number of plates of the distillation column in Example 1.

As a result, a plate having the highest water content was the top plate (water content of 2.8% by weight) of the column, and in the column hydrogen iodide was not condensed. The concentration of hydrogen iodide in the acetic acid distillate withdrawn from the side-cut was 40 ppm. FIG. 3 shows the distribution of the water content and the concentration of hydrogen iodide (HI concentration) in the column.

The invention claimed is:

1. A process for distilling a mixture containing hydrogen iodide and water, comprising: distilling the mixture in a distillation system using a distillation column,
    wherein the water content in the top of the column is maintained at a range of about 0.1 to 4% by weight, thereby preventing condensation of hydrogen iodide in the distillation system.

2. A process according to claim 1, wherein the water content In the top of the distillation column is 3% by weight or less.

3. A process according to claim 1, wherein the mixture contains hydrogen iodide, water, an alcohol having a carbon number of "n", an alkyl iodide corresponding to the alcohol, a carboxylic acid having a carbon number of "n+1", and an ester of the carboxylic acid with the alcohol.

4. A process for producing acetic acid comprising:
    distilling a mixture containing hydrogen iodide, water, methanol, methyl iodide, acetic acid and methyl acetate in a distillation column, wherein the water content in the top of the distillation column is maintained at a range of 5% by weight or less, thereby preventing condensation of hydrogen iodide in the distillation column,
    withdrawing a fraction containing. hydrogen iodide from the top of the column, and
    withdrawing acetic acid as a side-cut stream by side-cut or a stream from the bottom of the column.

5. A process for producing acetic acid comprising:

distilling a mixture containing hydrogen iodide, water, methanol, methyl iodide, acetic acid and methyl acetate in a distillation column, wherein the water content in the top of the distillation column is maintained at a range of 5% by weight or less, thereby preventing condensation of hydrogen iodide in the distillation column, withdrawing a fraction containing hydrogen iodide from the top of the column, and withdrawing acetic acid as a side-cut stream by side-cut or a stream from the bottom of the column to reduce the concentration of hydrogen iodide to not more than 50 ppm in said acetic acid.

6. A process according to claim 1, wherein the mixture contains hydrogen iodide at a concentration of 1 to 3000 ppm on the basis of weight.

7. A process according to claim 3, wherein at least one component selected from the group consisting of methanol, methyl acetate and an alkali metal hydroxide is introduced into the distillation column, and the mixture is distilled while maintaining the water content of about 0.1 to 4% by weight in the distillation column.

8. A process according to claim 4, wherein the mixture contains hydrogen iodide at a concentration of 1 to 3000 ppm on the basis of weight.

9. A process according to claim 5, wherein the mixture contains hydrogen iodide at a concentration of 1 to 3000 ppm on the basis of weight.

10. A process according to claim 4, wherein at least one component selected from the group consisting of methanol, methyl acetate and an alkali metal hydroxide is introduced into the distillation column, and the mixture is distilled while maintaining the water content of not more than 5% by weight in the distillation column.

11. A process according to claim 5, wherein at least one component selected from the group consisting of methanol, methyl acetate and an alkali metal hydroxide is introduced into the distillation column, and the mixture is distilled while maintaining the water content of not more than 5% by weight in the distillation column.

12. A process according to claim 1, wherein the mixture comprises a light component or fraction separated from a mixture obtained by carbonylation of an alcohol having a carbon number of "n", wherein the light component or fraction is separated in a previous distillation step in a flash distillation column.

13. A process according to claim 1, wherein the distillation column is a plate column or a packed column.

14. The process according to claim 4, wherein the water content in the top of the distillation column is maintained at a range of about 0.1 to 4% by weight.

15. The process according to claim 5, wherein the water content in the top of the distillation column is maintained at a range of about 0.1 to 4% by weight.

* * * * *